(12) United States Patent
Fuchs

(10) Patent No.: US 11,633,550 B2
(45) Date of Patent: Apr. 25, 2023

(54) DEVICE FOR DOSING LIQUID

(71) Applicant: F+K Innovationen Gmbh & Co. KG, Baden-Baden (DE)

(72) Inventor: Karl-Heinz Fuchs, Radolfzell (DE)

(73) Assignee: F+K Innovationen Gmbh & Co. KG, Baden-Baden (DE)

( * ) Notice: Subject to any disclaimer, the term of this patent is extended or adjusted under 35 U.S.C. 154(b) by 42 days.

(21) Appl. No.: 16/962,362

(22) PCT Filed: Jan. 16, 2019

(86) PCT No.: PCT/EP2019/051017
§ 371 (c)(1),
(2) Date: Jul. 15, 2020

(87) PCT Pub. No.: WO2019/141713
PCT Pub. Date: Jul. 25, 2019

(65) Prior Publication Data
US 2020/0345953 A1    Nov. 5, 2020

(30) Foreign Application Priority Data

Jan. 16, 2018 (DE) .................... 10 2018 100 847.3
Apr. 12, 2018 (DE) .................... 10 2018 108 700.4
Jul. 23, 2018 (DE) .................... 10 2018 117 731.3

(51) Int. Cl.
*A61M 11/00* (2006.01)
*A61F 9/00* (2006.01)

(52) U.S. Cl.
CPC ......... *A61M 11/007* (2014.02); *A61F 9/0008* (2013.01); *A61M 11/008* (2014.02);
(Continued)

(58) Field of Classification Search
CPC .............. A61M 11/007; A61M 11/008; A61M 2205/3337; A61M 2210/0612;
(Continued)

(56) References Cited

U.S. PATENT DOCUMENTS 3,043,305 A  *  7/1962  Walden ............... A61M 3/0291
                                                          604/106
5,261,571 A  *  11/1993 Goncalves ............. G01F 11/08
                                                          222/541.6
(Continued)

FOREIGN PATENT DOCUMENTS

CN       108498236 A  *  9/2018 ........... A61F 9/0008
DE       69210561 T2      1/1997
(Continued)

OTHER PUBLICATIONS

International preliminary report on patentability for application No. PCT/EP2019/051017 dated Jul. 21, 2020.
(Continued)

*Primary Examiner* — Tatyana Zalukaeva
*Assistant Examiner* — Hans Kaliher
(74) *Attorney, Agent, or Firm* — Bachman & LaPointe, P.C.

(57) ABSTRACT

The invention relates to a device for dosing liquid from a liquid-receiving element (2), in which the liquid-receiving element (2) comprises an outlet valve (1), and a dosing system is available, said dosing system consisting of a first actuating wing (4) and a second actuating wing (5), which are arranged around the liquid-receiving element (2) and can be moved in relation to each other such that they compress the liquid-receiving element (2), a mechanical dosing stop being available.

14 Claims, 13 Drawing Sheets

(52) U.S. Cl.
CPC .............. *A61M 2205/3337* (2013.01); *A61M 2210/0612* (2013.01)

(58) Field of Classification Search
CPC ... A61M 11/00; A61M 35/003; A61F 9/0008; B05B 11/00; B05B 11/0038; B05B 11/0044; B05B 11/04; B05B 11/3057; B05B 11/3045; B05B 11/048; B05B 11/3011; B05B 11/0032; B05B 11/0027
See application file for complete search history.

(56) References Cited

U.S. PATENT DOCUMENTS

| | | | | |
|---|---|---|---|---|
| 5,460,299 A * | 10/1995 | Prause | ................ | B65D 75/48 222/494 |
| 2002/0107493 A1* | 8/2002 | Cogger | ................ | A61F 9/0008 604/300 |
| 2005/0056664 A1* | 3/2005 | Wolter | ................ | B05B 1/3431 222/321.7 |
| 2006/0191959 A1* | 8/2006 | Davies | ................ | B05B 11/3056 222/402.15 |
| 2007/0164049 A1* | 7/2007 | Bonney | ................ | B05B 11/309 222/162 |
| 2009/0235923 A1* | 9/2009 | Nilson | ................ | A61M 15/009 239/533.13 |
| 2009/0259204 A1* | 10/2009 | Galdeti | ................ | A61F 9/0026 222/173 |
| 2011/0106024 A1* | 5/2011 | Katayama | ............. | A61F 9/0008 222/207 |
| 2012/0132199 A1* | 5/2012 | Kiesewetter | ........ | B05B 11/3015 128/200.22 |
| 2015/0336124 A1* | 11/2015 | Welp | ................ | B05B 11/3019 222/383.1 |

FOREIGN PATENT DOCUMENTS

| | | |
|---|---|---|
| FR | 2568007 A1 | 1/1986 |
| FR | 2859464 A1 | 3/2005 |
| GB | 246213 A | 2/2010 |
| RU | 2323749 C2 | 5/2008 |
| WO | 2008036974 A2 | 3/2008 |
| WO | 2013163364 A1 | 10/2013 |

OTHER PUBLICATIONS

International search report for patent application No. PCT/EP2019/051017 dated May 6, 2019.
German request for examination for application No. 10 2018 117 731.3 dated Feb. 18, 2021.

* cited by examiner

DEVICE FOR DOSING LIQUID

BACKGROUND OF THE INVENTION

The invention relates to a device for dosing liquid.

Such devices for dosing eye drop fluid are already known and used in many different forms and designs. In the WO 2017/162805 A1, for example, such a dosing device is disclosed, where an air valve is embedded in the outer wall of a bottle and a liquid bag is arranged inside the bottle.

SUMMARY OF THE INVENTION

The object of the present invention is to overcome the disadvantages of the prior art. In particular, a device is to be provided which enables an appropriate dosing while preventing the sprayed liquid from forming a jet when actuated.

The features disclosed herein lead to the solution of the object.

Advantageous configurations are described in the dependent claims.

A device for dosing liquid according to the invention is used for dispensing liquid from a liquid intake. Liquid intake here is a plastic bottle that can be squeezed together. The liquid intake includes an outlet valve. The outlet valve is designed in such a way, that the liquid can be discharged without allowing air to enter the liquid intake through the outlet valve.

A dosing system is provided for this purpose, the dosing system comprising a first actuating blade and a second actuating blade or a slotted sleeve being arranged around the liquid intake and the liquid intake being movable relative to one another in a compressive manner, whereby a mechanical dosing stop is provided. The mechanical dosing stop is provided in such a way that the two actuating blades can only be moved towards each other to a defined extent, or in the case of the slotted sleeve both halves can be moved towards each other in a defined manner.

The first actuating blade has a first finger support on the finger actuating flange and the second actuating blade has a finger support on the finger actuating flange. These finger supports are used for better use of the dosing system as well as to reduce the actuating force by extending the actuating path via the actuating blades.

Furthermore, the first actuating blade comprises a first connecting bar and the second actuating blade comprises a second connecting bar. In preferred embodiments, two first connecting bars and two second connecting bars can be arranged, which then encompass the liquid intake. The actuating blades of the slotted sleeve can also be designed without connecting bars.

The first connecting bar has a guide pin and the second connecting bar has an elongated hole. This is a mechanical dosing stop, as the guide pin is guided in a defined manner in the elongated hole and when the end of the elongated hole is reached, it is a mechanical stop. Furthermore, a mechanical stop can also be arranged on the blades or half-shells.

The system is always operated by the compressed air.

If the air valve or valve closure works well, there should always be a quantity of air trapped between the bag and the bottle wall. This means that the actuating stroke is approximately always the same. This means that changes in air volume concerning the bag emptying are not taken into account.

In order to generate a constant drop dosage without jet formation, an actuating path stop would be sufficient, i.e. stroke limitation for one drop size.

With an actuating blade, i.e. one of the actuating half-shells, which is anchored to the bottle in the form of the liquid intake and has an actuating path limiter, a constant drop dosage can be generated when actuating the actuating half-shells, and the actuating force can be reduced and jet formation prevented.

Furthermore, the first actuating blade comprises a first connecting bar and the second actuating blade comprises a second connecting bar. In preferred embodiments, two first connecting bars and two second connecting bars can be arranged, which then encompass the liquid intake.

The first connecting bar has a guide pin and the second connecting bar has an elongated hole. This is a mechanical dosing stop, as the guide pin is guided in a defined manner in the elongated hole and when the end of the elongated hole is reached, it is a mechanical stop.

The system is always operated by the compressed air.

In order to generate a constant drop dosage without jet formation, an actuating path stop would be sufficient, i.e. stroke limitation for one drop size.

For manufacturing reasons, the stop cannot be integrated into the inside of the bottle.

With an actuating blade, i.e. one of the actuating half-shells, which is anchored to the bottle in the form of the liquid intake and has an actuating path limiter, a constant drop dosage can be generated when actuating the actuating half-shells, and the actuating force can be reduced and jet formation prevented.

To protect the system from unintentional actuation, the protective flap has two pockets in which the finger actuation flanges engage when the protective cap is in place and thus prevent actuation when the protective cap is in place. This area can also be combined with a childproof closure.

The actuating blade or slotted sleeve can be contour pre-stressed for liquid intake or can be snap-fitted only or a combination of both, with the finger actuating area on the flange torsion-free with actuating clearance for liquid intake to allow the actuating path.

As an additional disassembly safety, the liquid intake has small recesses in which the actuating blades engage with the liquid intake when the actuating blades are mounted.

In order to enable the actuating blade the actuating path, both blades or half-shells are connected opposite the actuating area with a film hinge or with a hinge geometry.

In order to replace the separate air valve in the liquid intake, a conical round pin, which is arranged on the inner wall of the actuating blades and moves into the vent hole of the liquid intake wall when the blades are actuated and, via the conical shape, closes the system against air leakage, so that the trapped air can be compressed between the inner bag and the liquid intake wall and thus, by actuating the actuating blades, the medium can escape via the outlet valve.

This system design generates a part-reduced drop dosing system with low actuating force as an airless system without atmospheric access openings in a simple construction.

In a further exemplary embodiment of the device according to the invention for dosing liquid from a liquid intake and the liquid intake is assigned an outlet valve. Furthermore, a dosing system is present, whereat the dosing system in turn consisting of the first actuating blade and the second actuating blade, which are arranged around the liquid intake and can be moved towards each other to compress the liquid intake, whereat the first actuating blade having a first pressure piston and the second actuating blade having a second pressure piston, wherein a output chamber is expressable arranged by the pressure pistons movably mounted relative to one another and the two pressure pistons are arranged to be resettable by a spring element and/or partial springs. Here a particularly good and simple dosage is possible.

BRIEF DESCRIPTION OF THE FIGURES

Further advantages, features and details of the invention result from the following description of preferred embodiment and from the drawing; these show in.

DETAILED DESCRIPTION

Figure 1:
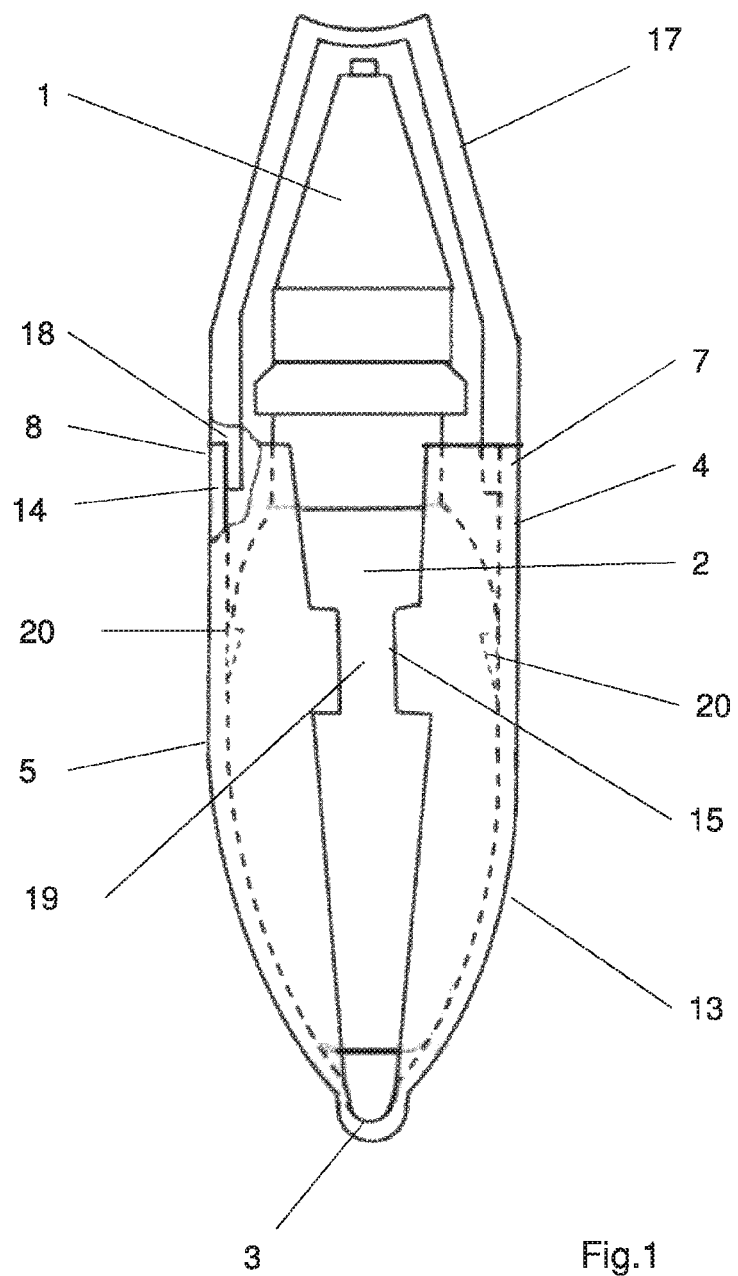
FIG. 1 a device according to the invention with protective cap.

In FIG. 1 a device according to the invention is shown in view and partly in section. The liquid intake 2 in the contour pre-stressed slotted sleeve 13 with the two actuating blades 4 and 5, which are movably connected via a film hinge 3 up to the hub stop 15. The recesses 20 in the liquid intake 2 accommodate the contour pre-stressed slotted sleeve 13 as a disassembly safeguard.

To protect the system against actuation, a protective cap 17 with two side pockets 18 for receiving the finger actuation flanges 14 with the finger supports 7 and 8 to prevent unintentional actuation of the system.

Figure 2:
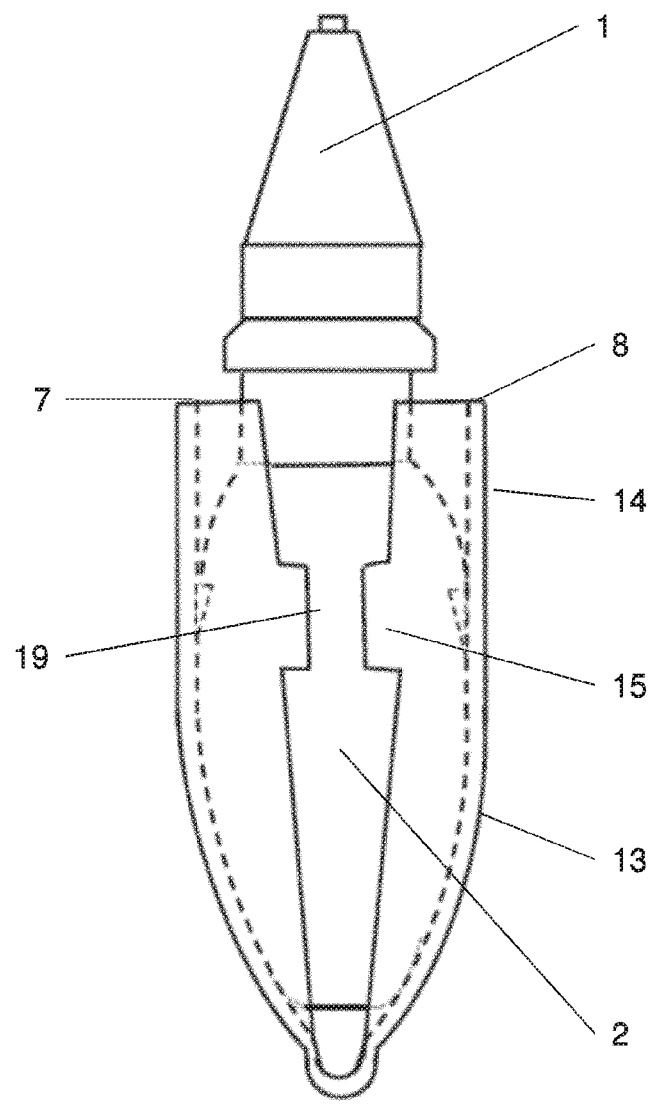
FIG. 2 a device according to the invention without protective cap.

FIG. 2 shows a device according to the invention in view without protective cap 17. The contour pre-stressed slotted sleeve 13 encases the liquid intake 2. At the upper end of the slotted sleeve 13 the two finger actuating flanges 14 are located with the finger supports 7 and 8 as actuating elements for the system.

Figure 3:
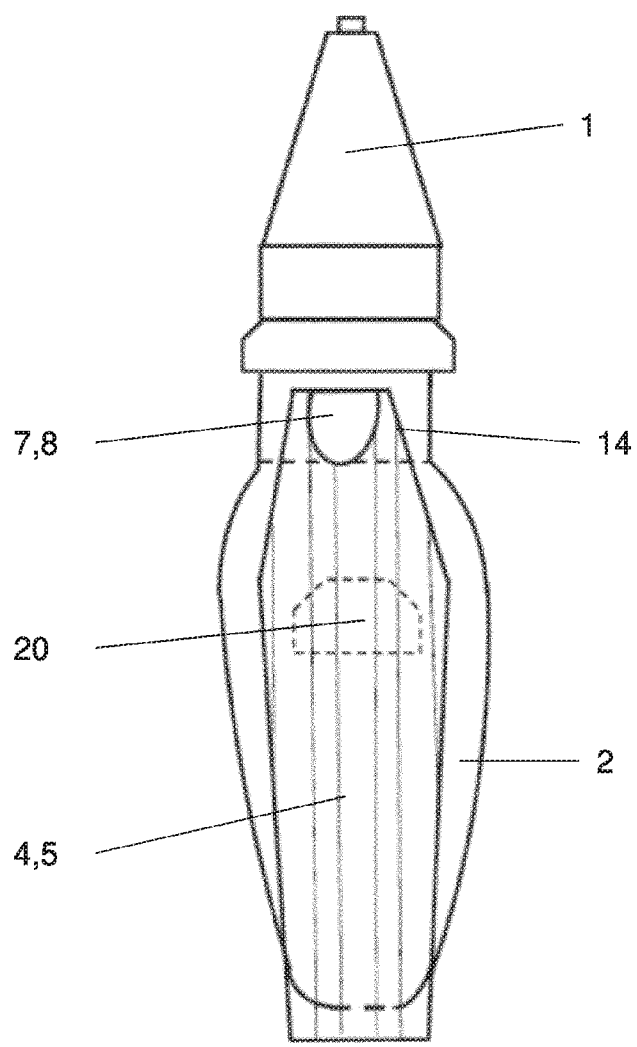
FIG. 3 a device according to the invention with the finger actuating flange.

FIG. 3 shows a device according to the invention as a view with the finger actuating flange 14, which with the actuating blades 4 and 5 encloses the liquid intake 2 via the recess 20 in a contour pre-stressed manner and the finger supports 7 and 8.

Figure 4:
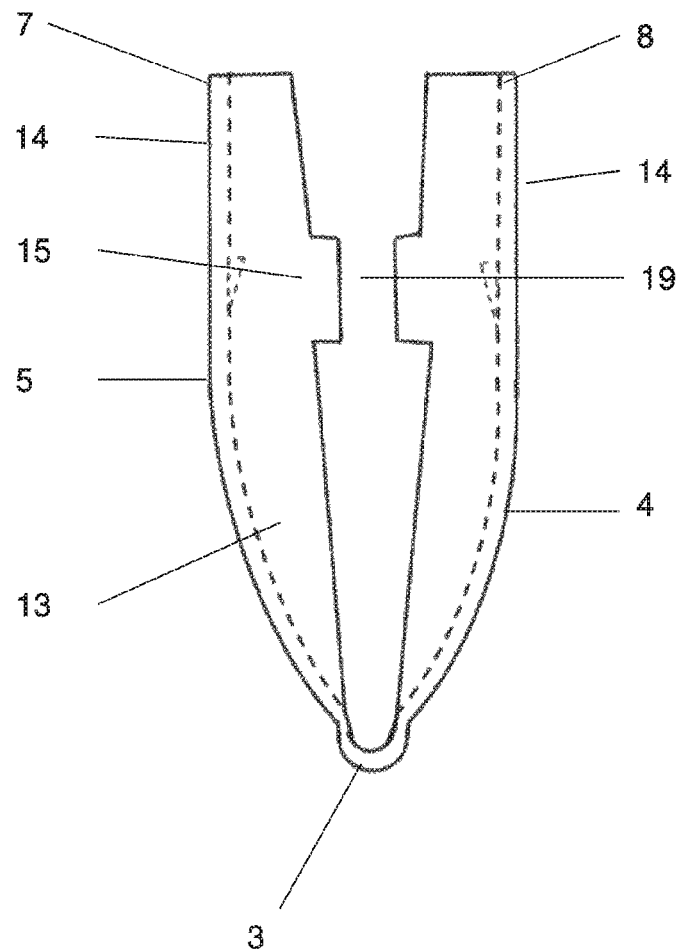
FIG. 4 a device according to the invention with slotted sleeve.

FIG. 4 shows the slotted sleeve 13 with the two actuating blades 4 and 5, the film hinge 3 and the actuating flanges 14 with the finger supports 7 and 8.

Figure 5:
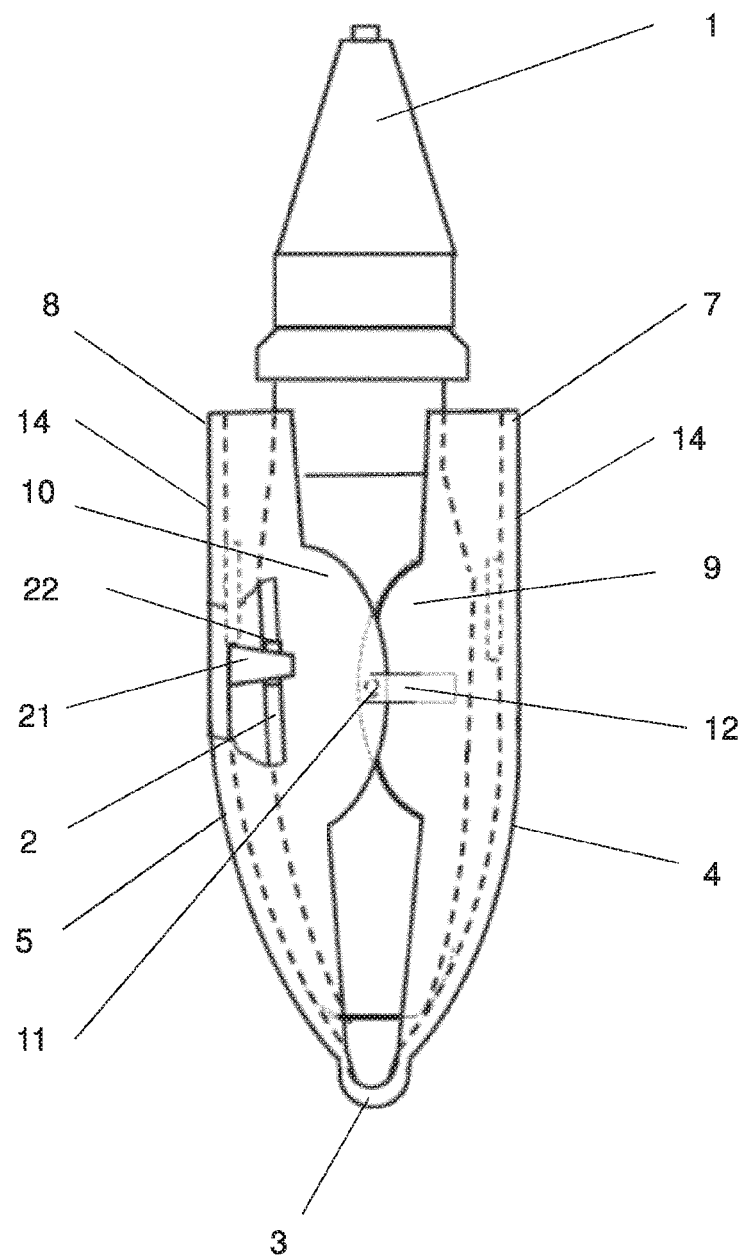
FIG. 5 a device according to the invention with the connecting bars.

FIG. 5 shows a device according to the invention in view without protective cap 17 as a snap-on design. The actuating blades 4 and 5, which are movably connected via the film hinge 3, are fixed and held in place by connecting bars 9 and 10 by the guide pin 11, which is arranged in an elongated hole 12 of the second connecting bar 10. On the opposite side of this view the same arrangement is symmetrically integrated. The partial section shows the conical round pin 21, which is located on the inner wall 6 of the actuating blade 4 or 5, which, when actuated via the finger actuating flanges 14 with the finger support 7 and 8, closes the vent hole 22 in the liquid intake wall 2 and, in the initial position, releases the hole for ventilation again.

Figure 6:
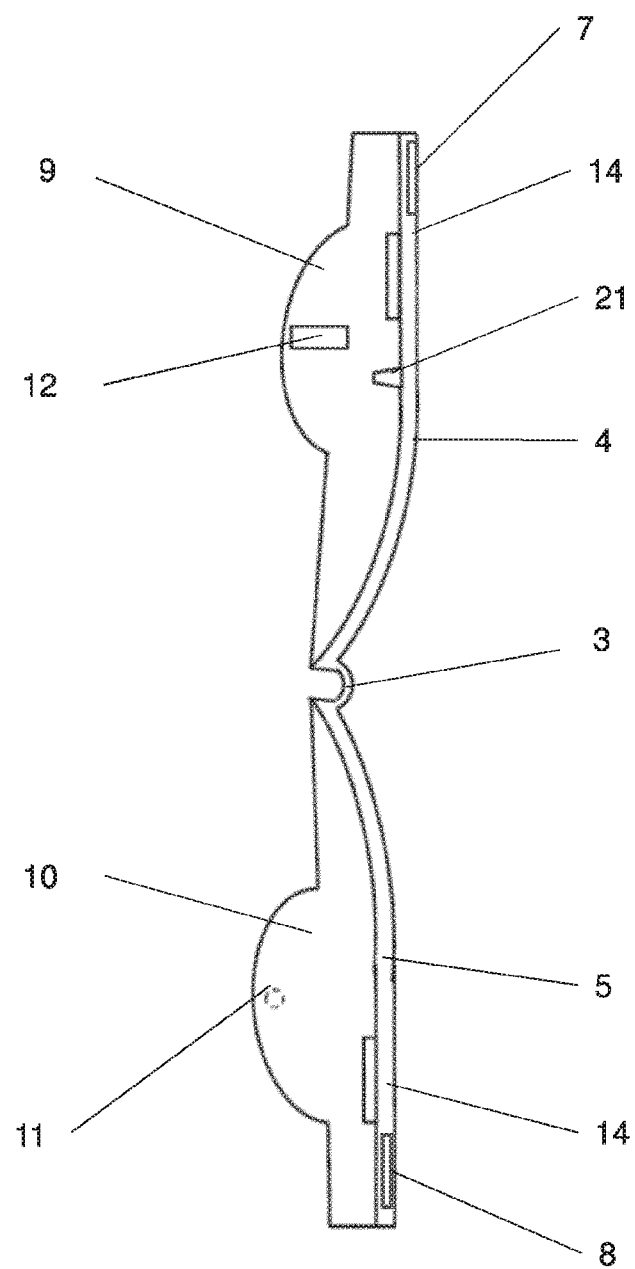
FIG. 6 a device according to the invention of the dosing system.

FIG. 6 shows the snapped system in unfolded condition. The two actuating blades 4 and 5, which are movably connected via the film hinge 3, merge into the finger actuating flange 14, which contains the finger supports 7 and 8. The connecting bars 9 and 10 as well as the guide pin 11 and the slotted hole 12 are integrated in the finger actuation flange 14.

Figure 7:
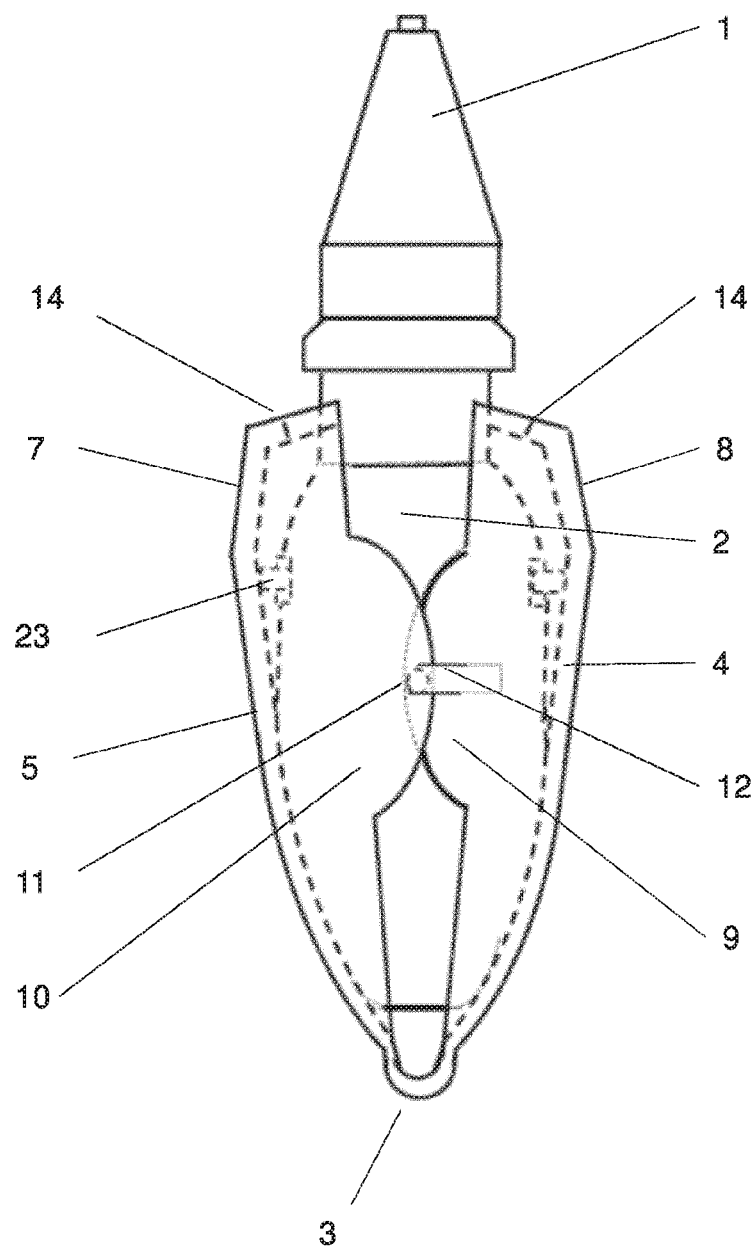
FIG. 7 a device according to the invention with the connecting bars and actuating stop.

FIG. 7 shows a device according to the invention in view without protective cap 17 as a snap-on version. The actuating blades 4 and 5, which are movably connected via the film hinge 3, are fixed together and held in position by connecting bars 9 and 10 through the guide pin 11, which are fixed together in the elongated hole 12 of the connecting bar 10. The actuating blades 4 and 5 reach into the liquid intake 2 via round element pin 23 and fix the system.

Figure 8:
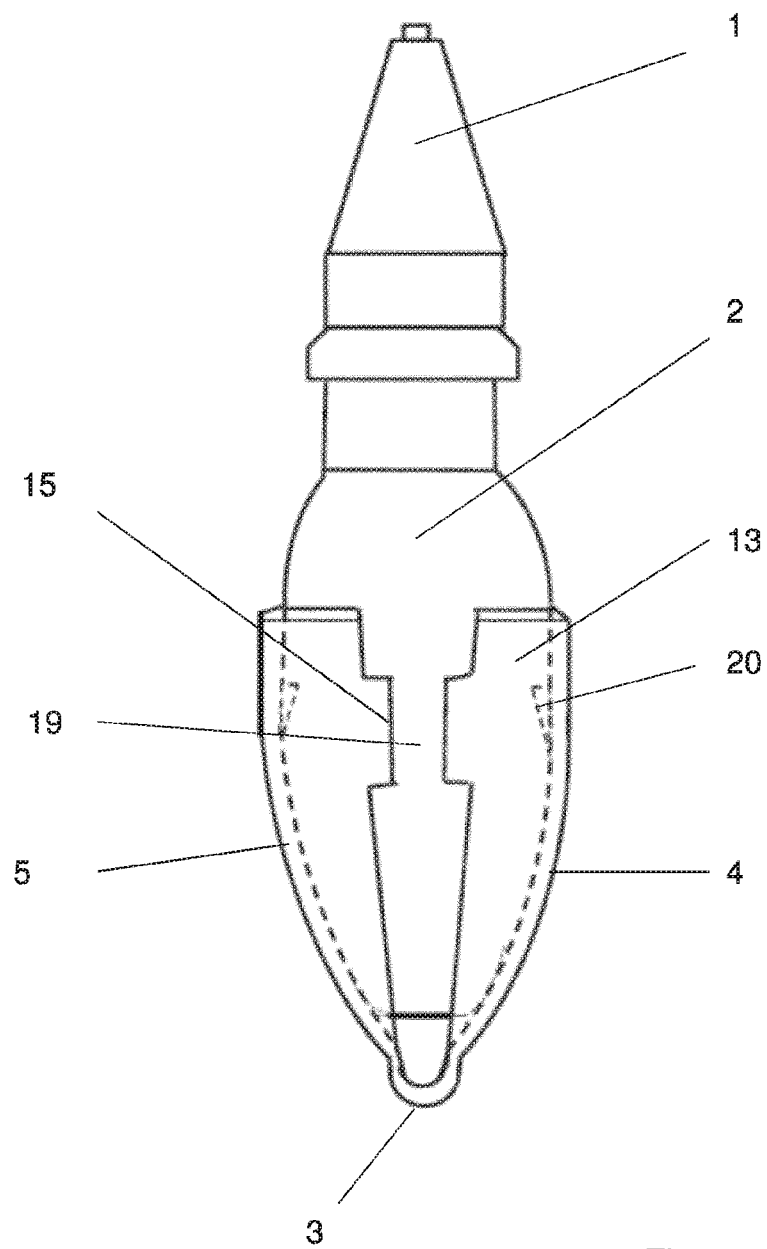
FIG. 8 a device according to the invention with slotted sleeve without actuating flange.

FIG. 8 shows a device according to the invention without protective cap 17. In this embodiment, the pre-stressed slotted sleeve 13 is shown without finger actuating flange 14, so that the actuation takes place directly via the sleeve wall.

Figure 9:
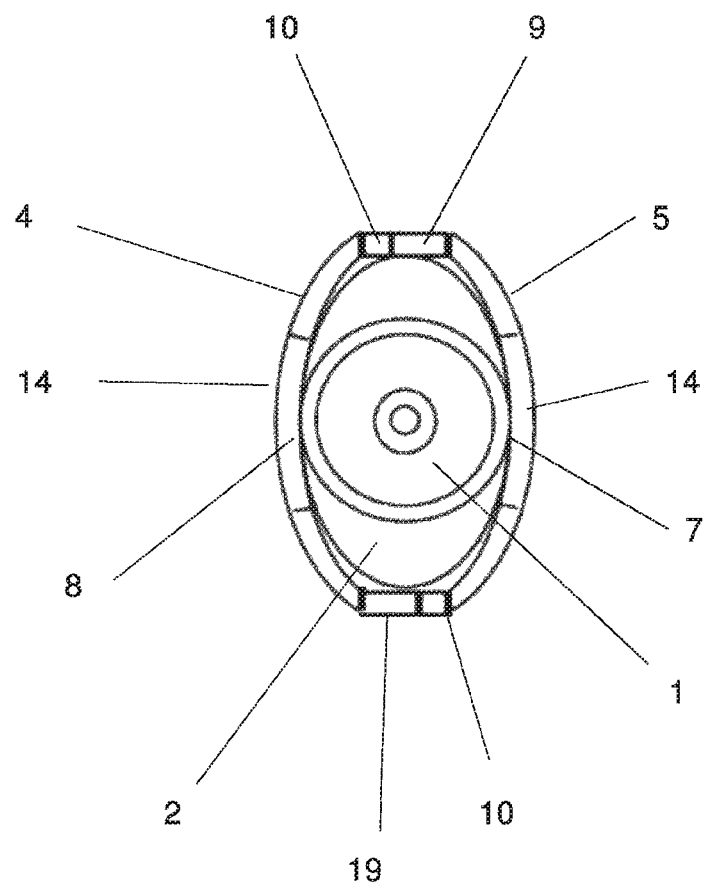
FIG. 9 a device according to the invention with connecting bars.

FIG. 9 shows the device according to the invention as a snap-on design in plan view with the two connecting bars 9 and 10, the two finger actuation flanges 14 with the finger supports 7 and 8 as well as with the outlet valve 1 with the liquid intake 2.

Figure 10:
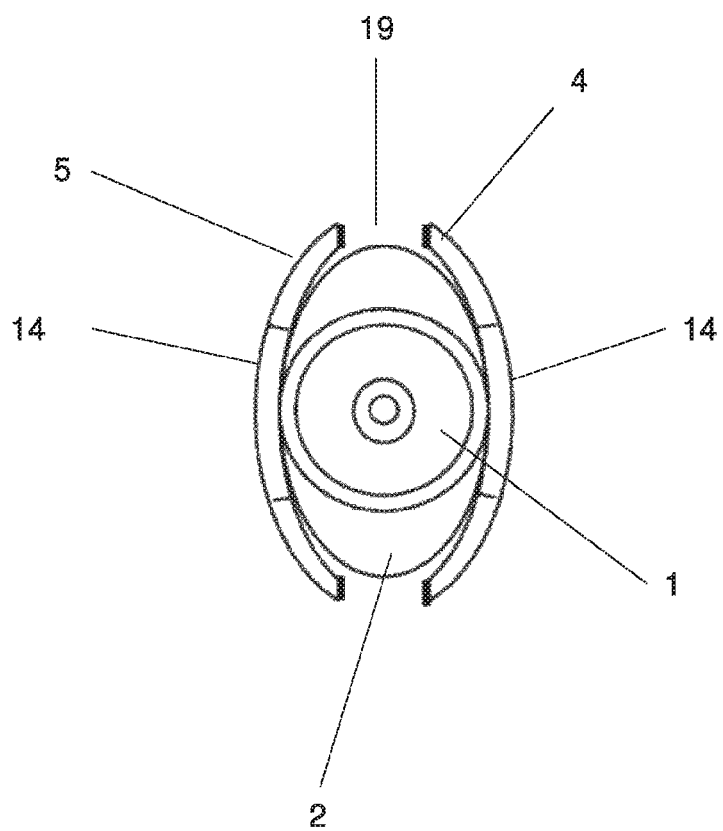
FIG. 10 a device according to the invention without connecting bars.

FIG. 10 shows the device according to the invention as a contour pre-stressed version in plan view with the two finger actuating flanges 14, the actuating blades 4 and 5 as well as the outlet valve 1 with the liquid intake 2. The actuating path 19 lays between the actuating blades 4 and 5.

Figure 11:
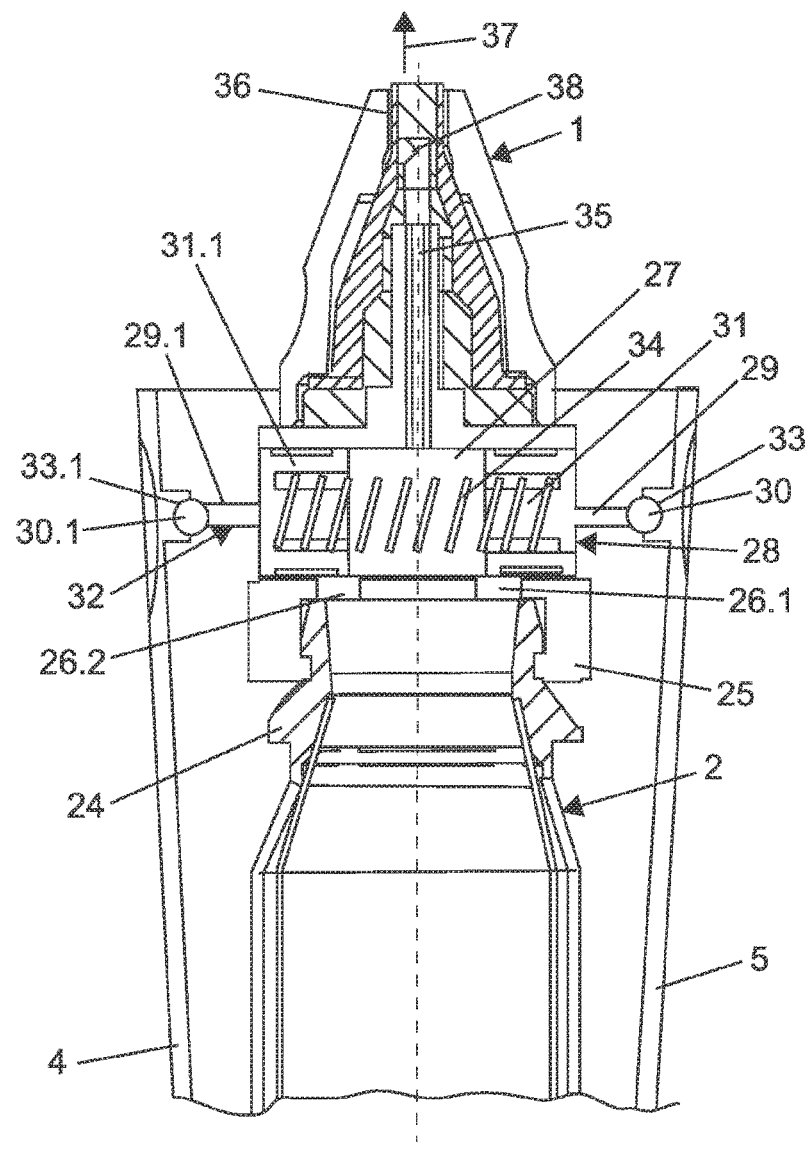
FIG. 11 shows a sectional side view of a part of a further exemplary embodiment.

FIG. 11 shows a sectional side view of a part of a further exemplary embodiment. There again the two actuating blades 4, 5 can be seen. The liquid intake 2 is located between the two actuating blades 4, 5. The liquid intake 2 has a neck clip 24. A valve clip 25 is provided on the neck clip 24. The valve clip 25 can be clipped onto the neck clip 24 and thus connects the valve 1 with the liquid intake 2. For this purpose, the valve clip 25 has two openings 26.1, 26.2, whereby the medium can be pressed out of the liquid intake 2 into a output chamber 27 through the two openings 26.1, 26.2.

The valve 1 has a sealing lip 36 which discharges the medium from a discharge channel 35 to the outside, as indicated by the arrow 37. The discharge channel 35 has a 90° turn 38 in the area of the sealing lip 36 towards the sealing lip 36.

Furthermore, the first actuating blade 4 includes a first pressure piston 28. The first pressure piston 28 in turn consists of a plunger 29, a joint head 30 and a compression element 31, while a second pressure piston 32 is shown in the same way, which in turn consists of a plunger 29.1, a joint head 30.1 and a compression element 31.1.

The joint head 30 is in turn received in a joint receiver 33, whereby the joint receiver 33 is designed as part of the second actuating blade 5. In the working position, the joint receiver 33 is designed towards the liquid intake 2. Working position means, if the liquid intake 2 is located between the two actuating blades 4, 5 and the medium can be pressed out.

In addition, the joint head 30.1 is in turn received in a joint receiver 33.1, whereby the joint receiver 33.1 is designed as part of the first actuating blade 4. In working position the joint receiver 33.1 is designed towards the liquid intake 2.

Furthermore a spring element 34 is shown, which is arranged between the first pressure piston 28 and the second pressure piston 32. After the two pressure pistons 28, 32 have been moved towards each other by the two actuating blades 4, 5 and the two compression elements 31, 31.1 have passed through the output chamber 27 towards each other in order to press the medium located there into a discharge channel 35, the spring element 34 returns the two compression elements 31, 31.1 to their initial position.

Subsequently, a negative pressure is created in the output chamber 27 and through the two openings 26.1, 26.2 new medium can flow from the liquid intake 2 into the output chamber 27. In this exemplary embodiment, the only spring element 34 is located between the first pressure piston 28 and the second pressure piston 32.

Figure 12:
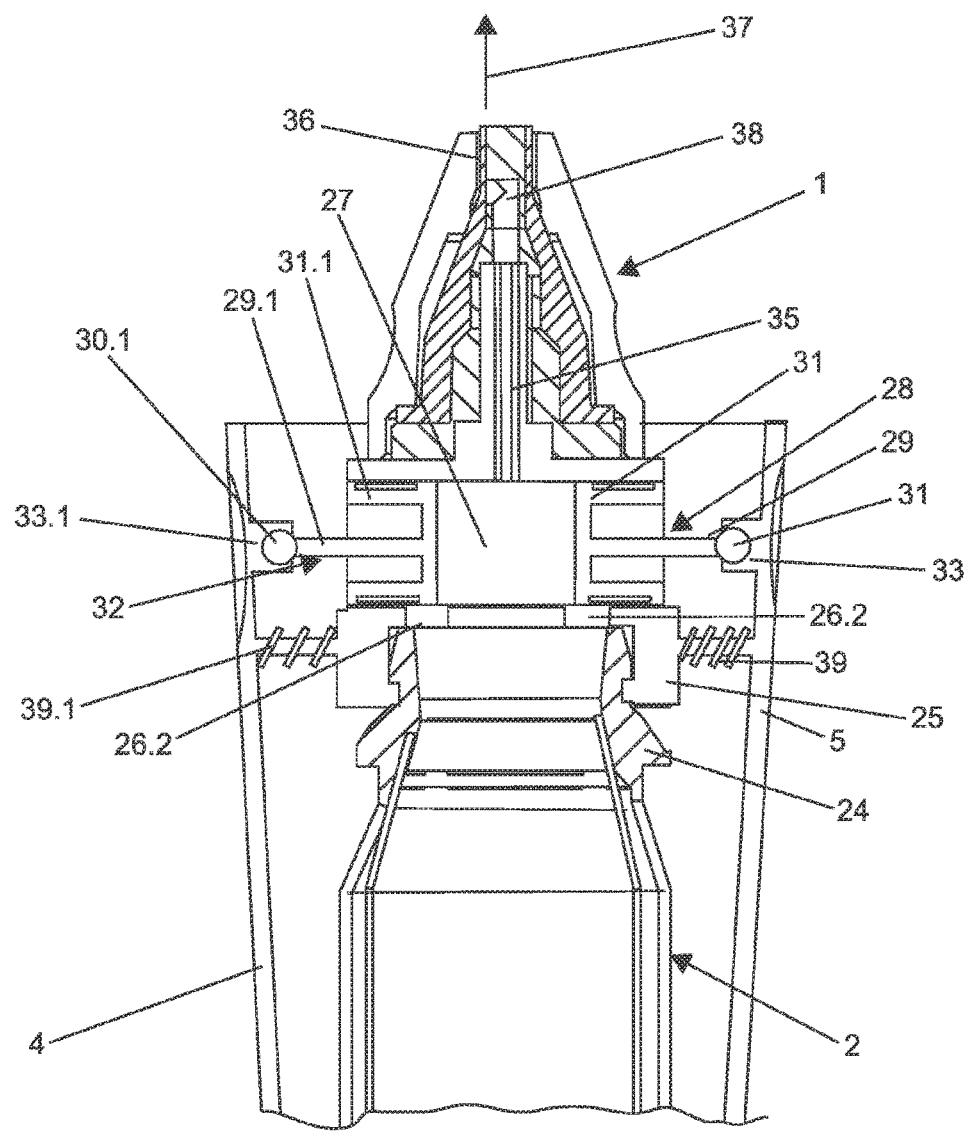
FIG. 12 shows a further view of an additional exemplary embodiment having two partial springs.

A further exemplary embodiment is shown in FIG. 12, whereby the explanations regarding the features in the previous figures also being intended to be readable on this figure. This applies in particular to features with identical reference numbers. No explicit repetition is made here.

Differently to FIG. 11, two partial springs 39, 39.1 are shown here. The first partial spring 39 is located between the second actuating blade 5 and the valve clip 25. Furthermore, the second partial spring 39.1 is located between the first actuating blade 4 and the valve clip 25.

Figure 13:
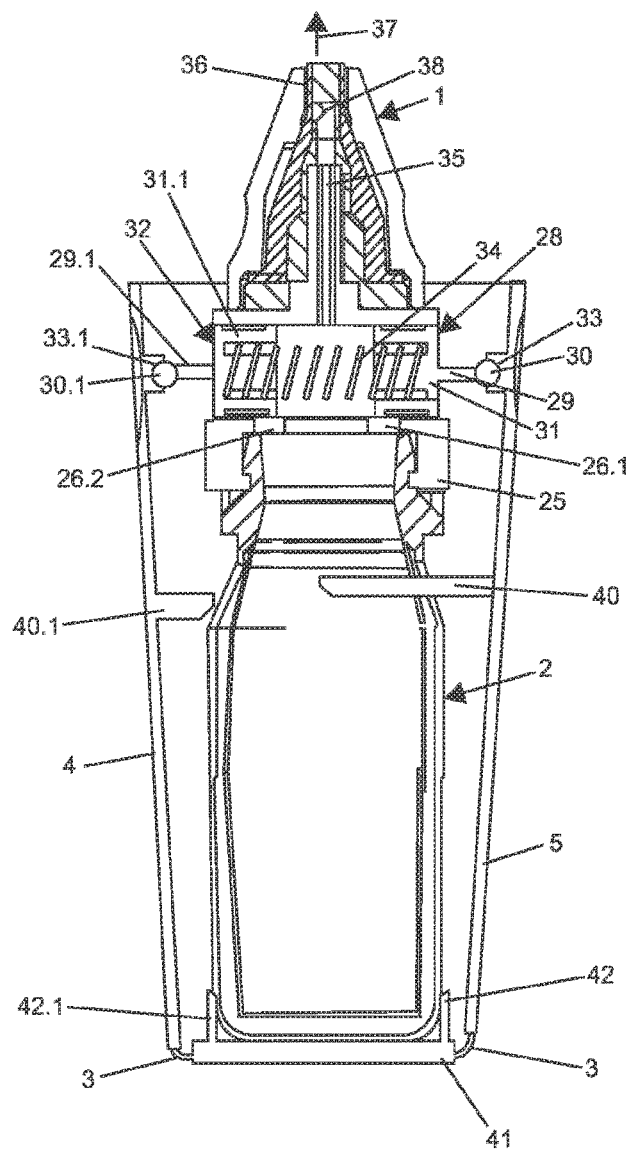
FIG. 13 shows a further view of an additional embodiment with additional features relating to holding pins and film hinges as well as base pins.

A further exemplary embodiment is shown in FIG. 13, whereby the explanations regarding the features in the previous figures also being intended to be readable on this figure. This applies in particular to features with identical reference numbers. No explicit repetition is made here.

Otherwise a first holding pin 40.1 is shown. In the working position, the first holding pin 40.1 projects away from the second actuating blade 5 in the direction of the liquid intake 2. Furthermore, a second holding pin 40.2 is also shown, which in turn is arranged in the working position away from the first actuating blade 4 towards the liquid intake 2. Both holding pins 40, 40.1 also partially extend beyond the liquid intake 2. Furthermore, two film hinges 3 are shown, which connect a base 41 with the two actuating blades 4, 5. Furthermore, the base 41 forms a first base pin 42 and a second base pin 42.1 in order to better hold the liquid intake 2 in the working position.

Although only a preferred embodiment of the invention has been described and presented, it is obvious that the skilled person can add numerous modifications without leaving the essence and scope of the invention. In particular, the skilled person may combine the combination of different features of different figures with each other within the limits of his skill. Without naming every single combination here.

REFERENCE LIST

| | |
|---|---|
| 1 | outlet valve |
| 2 | liquid intake |
| 3 | film hinge |
| 4 | first actuating blade |
| 5 | second actuating blade |
| 6 | inner wall |
| 7 | first finger support |
| 8 | second finger support |
| 9 | first connecting bar |
| 10 | second connecting bar |
| 11 | guide pin |
| 12 | elongated hole |
| 13 | slotted sleeve |
| 14 | finger actuating flange |
| 15 | hub stop |
| 16 | half shell |
| 17 | protective cap |
| 18 | pocket |
| 19 | actuating path |
| 20 | recess |
| 21 | conical round pin |
| 22 | vent hole |
| 23 | element pin |
| 24 | neck clip |
| 25 | valve clip |
| 26 | opening |
| 27 | output chamber |
| 28 | first pressure piston |
| 29 | plunger |
| 30 | joint head |
| 31 | compression element |
| 32 | second pressure piston |
| 33 | joint receiver |
| 34 | spring element |
| 35 | discharge channel |
| 36 | sealing lip |
| 37 | arrow |
| 38 | 90° turn |
| 39 | partial spring |
| 40 | holding pin |
| 41 | base |
| 42 | base pin |

The invention claimed is:

1. Device for dosing liquid from a liquid intake (2), wherein the liquid intake (2) comprises an outlet valve (1), wherein, a dosing system is provided, wherein the dosing system comprises a first actuating blade (4) and a second actuating blade (5) which are arranged around the liquid intake (2) and can be moved relative to one another in a compressive manner, wherein the first actuating blade (4) has a first pressure piston (28) and the second actuating blade (5) has a second pressure piston (32), wherein an output chamber (27) is arranged so as to be able to be compressed by the first and second pressure pistons (28, 32) which are movably mounted relative to one another and arranged in opposition to each other, and the first and second pressure pistons (28, 32) are resettably arranged by at least one spring element (34, 39, 39.1), wherein each of the first pressure piston (28) and the second pressure piston (32) comprises a plunger (29, 29.1), a rod end (30, 30.1) mounted to one of the first blade (4) and the second blade (5), and a spring element of the at least one spring element, and further comprising a valve clip (25) for securing the valve (1) to the liquid intake (2), wherein the valve clip (25) comprises openings (26.1, 26.2) allowing communication between the liquid intake (2) and the output chamber (27) when the first and second pressure pistons (28, 32) are in an open position.

2. Device according to claim 1, wherein the first actuating blade (4) and the second actuating blade (5) are connected via a film hinge (3) and are pivotable relative to one another.

3. Device according to claim 1, wherein the first actuating blade (4) and the second actuating blade (5) have an inner wall (6), the first actuating blade (4) having a first finger support (7) and the second actuating blade (5) having a second finger support (8).

4. Device according to claim 1, wherein the first actuating blade (4) comprises one of a first connecting bar (9) and a second connecting bar (10), and the second actuating blade (5) comprises the other of the first connecting bar (9) and the second connecting bar (10).

5. Device according to claim 4, wherein the first connecting bar (9) has a guide pin (11) and the second connecting bar (10) has an elongated hole (12) receiving the guide pin (11).

6. Device according to claim 1, further comprising a protective cap (17) with pockets (18).

7. Device according to claim 1, wherein two finger actuating flanges (14) are arranged at an upper end of a slotted sleeve (13) encasing the valve intake (2).

8. Device according to claim 1, wherein the actuating blades (4, 5) are in contact with a recess (20) of the liquid intake (2) in a contour pre-stressed manner.

9. Device according to claim 1, wherein the actuating blades (4, 5), are movably connected via a film hinge (3), and are fixed and movably held together via connecting bars (9, 10) and by a guide pin (11), which is arranged in an elongated hole (12) of one connecting bar (10) of the connecting bars (9, 10).

10. Device according to claim 1, wherein a conically round pin (21) is provided, which is located on an inner wall (6) of the actuating blades (4, 5), wherein upon actuation via finger actuating flanges (14) with finger supports (7, 8) a vent hole (22) in a wall of the liquid intake (2) is closed by the finger supports (7, 8) and in a starting position releases the hole again for ventilation.

11. Device according to claim 1, wherein the at least one spring element comprises a plurality of partial springs, and the pistons are resettably arranged by the plurality of partial springs (39, 39.1) wherein each piston is acted upon by one partial spring of the plurality of partial springs.

12. Device according to claim 1, wherein the valve (1) has a sealing lip (36) which discharges the medium from a discharge channel (35) to the outside.

13. Device according to claim 12, wherein the discharge channel (35) has a 90° turn (38) in an area of the sealing lip (36) and angled towards the sealing lip (36).

14. Device according to claim 1, wherein the first and second actuating blades (4, 5) are moveable relative to each other between an open position where they are spaced away from each other and the liquid intake (2), and a closed position wherein they are moved from the open position toward each other and the liquid intake (2), wherein movement from the open position to the closed position presses fluid from output chamber (27) to a discharge (37) of the nozzle (1), and wherein movement from the closed position to the open position draws fluid from the liquid intake (2) into the output chamber (27).

* * * * *